United States Patent
Fotheringham et al.

(10) Patent No.: US 6,358,714 B1
(45) Date of Patent: *Mar. 19, 2002

(54) MATERIALS AND METHODS FOR THE PRODUCTION OF D-PHENYLALANINE

(75) Inventors: Ian Fotheringham, Vernon Hills; Paul P. Taylor, Arlington Heights; Roberta K. Yoshida, Buffalo Grove, all of IL (US)

(73) Assignee: The Nutrasweet Company, Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/424,797

(22) Filed: Apr. 19, 1995

Related U.S. Application Data (63) Continuation-in-part of application No. 08/415,716, filed on Apr. 3, 1995, now abandoned.

(51) Int. Cl.$^7$ ................................................ C12P 13/22
(52) U.S. Cl. ........................................ 435/108; 435/106
(58) Field of Search ................................ 435/108, 193, 435/106; 536/23.2

(56) References Cited

U.S. PATENT DOCUMENTS

| | | | |
|---|---|---|---|
| 5,120,837 A | 6/1992 | Fotheringham et al. | ........ 536/27 |
| 5,354,672 A | 10/1994 | Fotheringham et al. | ...... 435/106 |
| 5,728,555 A | * 3/1998 | Fortheringham et al. | |

FOREIGN PATENT DOCUMENTS

WO   WO 91/05870 A1   5/1991

OTHER PUBLICATIONS

Nakajima et al. "Enantioselective synthesis of various D–amino acids by a multi–enzyme system" J. Biochemistry 8, 243–248, Jul. 1988.*

Doublet et al., Identification of the *Escherichia coli murI* Gene, Which Is Required for the Biosynthesis of D–Glutamic Acid, a Specific Component of Bacterial Peptidoglycan, *J. Bacteriol.*, 174(18):5772–5579 (Sep. 1992).

Hamilton, "The Clinical Immunology Laboratory of the Future", *Clin. Chem.*, 40(11B):2186–2192 (1994).

Lugtenburg et al., "Properties of a D–Glutamic Acid–Requiring Mutant of *Escherichia coli*", *J. Biol. Chem.*, 114(2):499–506 (May 1973).

Martinez del Pozo, et al., "Stereospecificity of Reactions Catalyzed by Bacterial D–Amino Acid Transaminase", *J. Biol. Chem.*, 264:17784–17789 (1989).

Martinez–Carrion and Jenkins, "D–Alanine–D–Glutamate Transaminase", *J. Biol. Chem.*, 240(9):3538–3546.

Meister, ed., Biochemistry (vol. 2—"Transaminasas") pp. 464–465, A Wiley–Interscience Publication, New York (1985).

Nakamura et al., "Factors Influencing Changes in the Clinical Immunology Laboratory", *Clin. Chem.*, 40(11B):2193–2204 (1994).

Pucci et al., "*Staphylococcus haemolyticus* Contains Two D–Glutamic Acid Biosynthetic Activities, a Glutamamte Racemase and a D–Amino Acid Transaminase", *J. Bacteriol.*, 177(2):336–342 (Jan. 1995).

Stoddard et al., "Preliminary X–Ray Data for a D–Amino Acid Amino–transferase from a Novel Thermophilic Bacillus", *J. Mol. Biol.*, 196:441–442 (1987).

Tanizawa et al., "The Primary Structure of the Thermostable D–Amino Acid Aminotransferase from a Thermophilic Bacillus Species and Its Correlation with L–Amino Acid Aminotransferases", *J. Biol. Chem.*, 264(5):2450–2453 (1989).

Tanizawa et al., "Thermostable D–Amino Acid Aminotransferase from a Thermophilic Bacillus Species", *J. Biol. Chem.*, 264(5)2445–2449 (Feb. 15, 1989).

Yonaha et al., "D–Amino Acid Aminotransferase of *Bacillus sphaericus*", *J. Biol. Chem.*, 250(17):6983–6988 (1975).

* cited by examiner

*Primary Examiner*—Nashaat T. Nashed
(74) *Attorney, Agent, or Firm*—Marshall, Gerstein, & Borun (57) ABSTRACT

The present invention provides materials and methods for production of D-phenylalanine by recombinant expression in a microorganisms of a D-aminotransferase gene and optionally a dadX gene in optional combination with eliminating or reducing expression of L-transaminase genes.

12 Claims, 6 Drawing Sheets

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
    (A) LENGTH: 95 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:1:

```
AAGCTTTTTT GTTGACAGCG TGAAAACAGT ACGGGTATAA TACTAAAGTC ACAAGGAGGA      60

TCCACTATGA CATCGGAAAA CCCGTTACTG GCGCT                                 95
```

(2) INFORMATION FOR SEQ ID NO:2:

(i) SEQUENCE CHARACTERISTICS:
        (A) LENGTH: 1424 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 427..1278

(xi) SEQUENCE DESCRIPTION: SEQ ID NO:2:

```
ACAAGGAGGA TCCGTTAATC CAAACGTTAG CTGGTGTTTA TCGCCGACAA ACGGGCGATA      60

ACGAAACACC TTTACTTTCA ACAGGCGGTG GAACGTATGC ACGCGTCTTG AAAAAAGGTG     120

TGGCATTCGG CATGCTTTTC CCTGGTGATC CAGATGTCAT GCATCGTGCG GATGAATATG     180

TAATTGTTGA TAAATTAGTA CAAGCTGCTG CTATTTATGC AGAAGCCATT GCAGAACTGG     240

CTGGGAAGTA AGTGTCATTA AGAGCGTAAT GTTTTCTTGC CAAAGAGATC ACGAAGCTTC     300

ACACGCCAAG CACTTCACTG AAAAATCTAC TTTGATTTAC TGCATCTGGT CTTACTTGAT     360

CGTCTAGTGG GAATCATTGT ACTTAAAAAT GTGAAAATAA CTTAAAAATG AAAAGGATGT     420
```

| ATAAAC | ATG | GCA | TAC | TCA | TTA | TGG | AAT | GAC | CAA | ATC | GTT | GAA | GAA | GGA | 468 |
|        | Met | Ala | Tyr | Ser | Leu | Trp | Asn | Asp | Gln | Ile | Val | Glu | Glu | Gly |     |
|        | 1   |     | 5   |     |     |     |     |     | 10  |     |     |     |     |     |     |

| TCT | ATT | ACA | ATT | TCA | CCA | GAA | GAC | CGT | GGT | TAT | CAA | TTT | GGT | GAT | GGT | 516 |
| Ser | Ile | Thr | Ile | Ser | Pro | Glu | Asp | Arg | Gly | Tyr | Gln | Phe | Gly | Asp | Gly |     |
| 15  |     |     |     | 20  |     |     |     |     | 25  |     |     |     |     | 30  |     |     |

| ATT | TAC | GAA | GTA | ATC | AAA | GTA | TAT | AAC | GGG | CAT | ATG | TTT | ACA | GCA | CAA | 564 |
| Ile | Tyr | Glu | Val | Ile | Lys | Val | Tyr | Asn | Gly | His | Met | Phe | Thr | Ala | Gln |     |
|     |     |     |     | 35  |     |     |     |     | 40  |     |     |     |     | 45  |     |     |

| GAG | CAC | ATC | GAT | CGT | TTC | TAT | GCT | AGT | GCC | GAA | AAA | ATT | CGC | CTT | GTT | 612 |
| Glu | His | Ile | Asp | Arg | Phe | Tyr | Ala | Ser | Ala | Glu | Lys | Ile | Arg | Leu | Val |     |
|     |     | 50  |     |     |     |     | 55  |     |     |     |     | 60  |     |     |     |     |

| ATT | CCT | TAT | ACA | AAA | GAT | GTA | TTA | CAC | AAA | TTA | TTG | CAT | GAT | TTA | ATC | 660 |
| Ile | Pro | Tyr | Thr | Lys | Asp | Val | Leu | His | Lys | Leu | Leu | His | Asp | Leu | Ile |     |
|     | 65  |     |     |     |     | 70  |     |     |     |     | 75  |     |     |     |     |     |

| GAA | AAA | AAT | AAT | TTA | AAT | ACA | GGT | CAT | GTT | TAC | TTC | CAA | ATT | ACA | CGT | 708 |
| Glu | Lys | Asn | Asn | Leu | Asn | Thr | Gly | His | Val | Tyr | Phe | Gln | Ile | Thr | Arg |     |
| 80  |     |     |     |     | 85  |     |     |     |     | 90  |     |     |     |     |     |     |

| GGA | ACA | ACT | TCT | CGT | AAC | CAC | ATT | TTC | CCG | GAT | GCA | AGC | GTA | CCA | GCA | 756 |
| Gly | Thr | Thr | Ser | Arg | Asn | His | Ile | Phe | Pro | Asp | Ala | Ser | Val | Pro | Ala |     |
| 95  |     |     |     |     | 100 |     |     |     |     | 105 |     |     |     |     | 110 |     |

| GTG | CTA | ACA | GGT | AAT | GTT | AAA | ACT | GGT | GAA | CGT | TCA | ATT | GAA | AAT | TTC | 804 |
| Val | Leu | Thr | Gly | Asn | Val | Lys | Thr | Gly | Glu | Arg | Ser | Ile | Glu | Asn | Phe |     |
|     |     |     |     | 115 |     |     |     |     | 120 |     |     |     |     | 125 |     |     |

| GAA | AAA | GGC | GTA | AAA | GCG | ACA | TTG | GTT | GAA | GAT | GTT | CGT | TGG | TTA | CGT | 852 |

```
Glu Lys Gly Val Lys Ala Thr Leu Val Glu Asp Val Arg Trp Leu Arg
                130                 135                 140

TGT GAT ATT AAA TCT TTA AAT TTA CTT GGC GCG GTA CTT GCG AAA CAA         900
Cys Asp Ile Lys Ser Leu Asn Leu Leu Gly Ala Val Leu Ala Lys Gln
            145                 150                 155

GAA GCA TCT GAA AAA GGT TGT TAC GAA GCC ATT TTA CAC CGT GGA GAT         948
Glu Ala Ser Glu Lys Gly Cys Tyr Glu Ala Ile Leu His Arg Gly Asp
        160                 165                 170

ATT ATC ACA GAA TGT TCT TCT GCT AAT GTC TAT GGT ATT AAA GAT GGT         996
Ile Ile Thr Glu Cys Ser Ser Ala Asn Val Tyr Gly Ile Lys Asp Gly
175                 180                 185                 190

AAA CTT TAT ACG CAC CCA GCA AAT AAC TAC ATC TTA AAT GGT ATT ACA        1044
Lys Leu Tyr Thr His Pro Ala Asn Asn Tyr Ile Leu Asn Gly Ile Thr
                195                 200                 205

CGC CAA GTT ATA TTA AAA TGT GCC GCT GAA ATA AAT TTA CCA GTG ATT        1092
Arg Gln Val Ile Leu Lys Cys Ala Ala Glu Ile Asn Leu Pro Val Ile
            210                 215                 220

GAA GAG CCG ATG ACA AAA GGC GAT TTA TTA ACA ATG GAT GAA ATT ATT        1140
Glu Glu Pro Met Thr Lys Gly Asp Leu Leu Thr Met Asp Glu Ile Ile
        225                 230                 235

GTG TCT TCT GTT TCA TCT GAA GTG ACA CCG GTT ATC GAT GTG GAT GGT        1188
Val Ser Ser Val Ser Ser Glu Val Thr Pro Val Ile Asp Val Asp Gly
240                 245                 250

CAG CAA ATT GGT GCA GGT GTT CCT GGT GAA TGG ACT CGT AAA TTG CAA        1236
Gln Gln Ile Gly Ala Gly Val Pro Gly Glu Trp Thr Arg Lys Leu Gln
255                 260                 265                 270

AAA GCA TTT GAG GCA AAA TTA CCA ATT TCA ATT AAT GCC TAATCTGTAT         1285
Lys Ala Phe Glu Ala Lys Leu Pro Ile Ser Ile Asn Ala
                275                 280

AAATGATTAA AAAGAGCTAC CTAAAACTTG GTTATTCGCC AAGTTAGGAG GGTAGCTCTT     1345

TTTTATAGAA CAAATATATGC ATGTATTCTC CTGAAACGTC ATGTAAAATA AAAAAGATAG    1405

CGCCTTTAGT CGATATCAC                                                 1424

(2) INFORMATION FOR SEQ ID NO:3:

(i) SEQUENCE CHARACTERISTICS:
        (A) LENGTH: 283 amino acids
        (B) TYPE: amino acid
        (D) TOPOLOGY: linear (ii) MOLECULE TYPE: protein (xi) SEQUENCE DESCRIPTION: SEQ ID NO:3:

Met Ala Tyr Ser Leu Trp Asn Asp Gln Ile Val Glu Glu Gly Ser Ile
1               5                   10                  15

Thr Ile Ser Pro Glu Asp Arg Gly Tyr Gln Phe Gly Asp Gly Ile Tyr
                20                  25                  30

Glu Val Ile Lys Val Tyr Asn Gly His Met Phe Thr Ala Gln Glu His
            35                  40                  45

Ile Asp Arg Phe Tyr Ala Ser Ala Glu Lys Ile Arg Leu Val Ile Pro
        50                  55                  60

Tyr Thr Lys Asp Val Leu His Lys Leu Leu His Asp Leu Ile Glu Lys
65                  70                  75                  80

Asn Asn Leu Asn Thr Gly His Val Tyr Phe Gln Ile Thr Arg Gly Thr
                85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
```

-continued

```
                        115                 120                     125
Gly Val Lys Ala Thr Leu Val Glu Asp Val Arg Trp Leu Arg Cys Asp
    130                 135                 140
Ile Lys Ser Leu Asn Leu Leu Gly Ala Val Leu Ala Lys Gln Glu Ala
145                 150                 155                 160
Ser Glu Lys Gly Cys Tyr Glu Ala Ile Leu His Arg Gly Asp Ile Ile
                165                 170                 175
Thr Glu Cys Ser Ser Ala Asn Val Tyr Gly Ile Lys Asp Gly Lys Leu
                180                 185                 190
Tyr Thr His Pro Ala Asn Asn Tyr Ile Leu Asn Gly Ile Thr Arg Gln
                195                 200                 205
Val Ile Leu Lys Cys Ala Ala Glu Ile Asn Leu Pro Val Ile Glu Glu
    210                 215                 220
Pro Met Thr Lys Gly Asp Leu Leu Thr Met Asp Glu Ile Ile Val Ser
225                 230                 235                 240
Ser Val Ser Ser Glu Val Thr Pro Val Ile Asp Val Asp Gly Gln Gln
                245                 250                 255
Ile Gly Ala Gly Val Pro Gly Glu Trp Thr Arg Lys Leu Gln Lys Ala
                260                 265                 270
Phe Glu Ala Lys Leu Pro Ile Ser Ile Asn Ala
                275                 280
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: amino acid     (xi) SEQUENCE DESCRIPTION: SEQ ID NO:4:

Val Ile Phe Tyr Leu Ala Leu                    7

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: amino acid     (xi) SEQUENCE DESCRIPTION: SEQ ID NO:5:

Leu Pro Ile Ser Ile Asn Ala                     7

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:6:

CGCAGATCTA CTATGGCATA CTCATTATGG                    30

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CATGCCATGG ATCCTCCTTT TAGGTAGCTC TTTTTAATC                              39

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CGCGGATCCA CTATGACCCG TCCGATACAG GCC                                   33

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TGCCATGCAT GCCTACAGTT GCTGACCAGC CGG                                   33

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CGCGGATCCT CGTCATGAAC AGAACTGACG AACTCCG                               37

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

ACGCGTCGAC TCAGAAGCGG GTATCTACCG CAGAGG                                36

(2) INFORMATION FOR SEQ ID NO:12:

(i) SEQUENCE CHARACTERISTICS:
        (A) LENGTH: 34 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:12:

GGAAGATCTT ACATCATCAA CCAGATCGAT TCTG                              34

(2) INFORMATION FOR SEQ ID NO:13:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

CGCGGATCCA TTATGGTTAC AGAAGGGAAG TCC                               33

(2) INFORMATION FOR SEQ ID NO:14:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

CCGCTCGAGC CCGACGCACT TTGCGCCGA                                    29

(2) INFORMATION FOR SEQ ID NO:15:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

CCCAAGCTTA TCAGGCTCTG GGAGGCAG                                     28

(2) INFORMATION FOR SEQ ID NO:16:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

GGAAGATCTA CTATGGAGAA TTTTTTCAGT ATTTTAGG                          38

(2) INFORMATION FOR SEQ ID NO:17:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA
```

-continued (xi) SEQUENCE DESCRIPTION: SEQ ID NO:17:

GCGGGATCCT CCTTTTCTAC TTTTCAGATA CTGTATCTAA TGC                43

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GGAAGATCTA CTATGCGCGT TAACAATGGT TTGACC                        36

(2) INFORMATION FOR SEQ ID NO:19:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GCGGGATCCT CCTTTGGGCC CTTATCCAGC GAACCGTGAG ATGCG              45

MATERIALS AND METHODS FOR THE PRODUCTION OF D-PHENYLALANINE

This application is a continuation-in-part of U.S. Ser. No. 08/415,716 filed Apr. 3, 1995, now abandoned.

FIELD OF THE INVENTION

The present invention generally relates to materials and methods for production of D-amino acids and specifically D-phenylalanine.

BACKGROUND OF THE INVENTION

With the exceptions of glycine, threonine, and isoleucine, each of the common, naturally-occurring amino acids exist as one of two optical isomers, termed levorotatory or dextrorotatory, depending upon the direction in which they cause the plane of plane-polarized light to rotate. Glycine, having no asymmetric carbon, has no optical isomers. Threonine and isoleucine, each having two asymmetric carbons, have four optical isomers each. Some amino acids, such as alanine and glutamine are dextrorotatory, producing a positive rotation. Others, such as phenylalanine and tryptophan, are levorotatory, producing a negative (left-handed) rotation. Thus, amino acids may be referred to as l- or d-amino acids in order to reflect their chirality in isolation.

The specific rotation produced by a given amino acid varies with temperature and pH. Accordingly, by convention, amino acids are also referred to as D or L (as opposed to the d or l designations referred to above) based upon whether the configuration about the α-carbon of amino acid corresponds to the D or L stereoisomer (enantiomer) of glyceraldehyde, the arbitrary standard. Based upon that standard, most naturally-occurring amino acids are L-amino acids, despite the fact that certain of them are dextrorotatory (d) when placed in aqueous solution at neutral pH. Most enzymes which act upon amino acids have asymmetric binding domains which recognize only the L-form of the amino acid. Accordingly most naturally-occurring proteins comprise L-amino acids.

There are, however, exceptions wherein D-amino acids are produced and utilized by cells. Principal among these is the production of D-glutamate and D-alanine by certain microorganisms. D-glutamate and D-alanine are primarily produced in bacterial cells and are utilized in murein synthesis. In the absence of D-glutamate and D-alanine, a defective bacterial cell wall is produced, resulting in cell lysis. Most bacteria produce D-amino acids not by direct synthesis, but through conversion of the corresponding L-amino acid by an amino acid-specific racemase. For example, many bacterial cells possess an alanine racemase which catalyzes bidirectional conversion between L-alanine and D-alanine, resulting in a racemic (50:50) mixture. Similarly, a glutamate racemase produces a racemic mixture of D-glutamate and L-glutamate, the former for incorporation into the cell wall and the latter for, inter alia, formation of protein. The specificity of those two enzymes is demonstrated by the fact that the lack of either one results in cell lysis due to defective cell wall formation.

Certain bacteria, such as members of the genus Bacillus, possess an alternative to racemases for making D-amino acids in the form of D-aminotransferases. Such an enzyme reversibly catalyzes the transamination of various D-amino acids and corresponding α-keto acids. In PCT Publication WO 91/05870, Manning reports a method for chemical synthesis of D-alanine and D-glutamate via catalysis by an aminotransferase. While Manning reports, at page 2, the use of a *Bacillus sphaericus* D-aminotransferase, that publication actually only reports the cloning, isolation, and use of a thermophilic species of D-aminotransferase which is not capable of effectively catalyzing synthesis of more than trace amounts of D-phenylalanine. Moreover, Manning fails to report any means for isolating or using a *B. sphaericus* D-aminotransferase or any other D-aminotransferase which catalyzes synthesis of D-phenylalanine.

Evidence that Manning's reference to a *B. sphaericus* D-aminotransferase is an error is found at page 2 of the Manning publication, wherein Manning states that the D-aminotransferase DNA was cloned onto plasmid pICT113. As reported in Stoddard, et al., *J. Mol. Biol.*, 196: 441–442 (1987), plasmid pICT113 carries the thermophilic species of D-aminotransferase and not the *B. sphaericus* species. The significance of that fact is that the thermophilic species cannot effectively catalyze significant production of D-phenylalanine and, therefore, is useless in recombinant methods for its production.

Prior to the present application, the only report of a *B. sphaericus* D-aminotransferase is a partial C-terminal sequence found in *Transaminases*, Christen, et al. (eds.), 464 (1985). However, as will be apparent from the present invention (See SEQ ID NO: 2), that partial sequence is wrong and is not useful in isolating the *B. sphaericus* D-aminotransferase. Accordingly, no prior reference reports a *B. sphaericus* D-aminotransferase gene sequence or the use of a *B. sphaericus* D-aminotransferase in the production, by recombinant means or otherwise, of a D-amino acid. Other D-aminotransferases have been isolated but, unlike the *Bacillus sphaericus* species, D-phenylalanine is a relatively poor substrate for those enzymes. Tanizawa, et al., *J. Biol. Chem.*, 264: 2445–2449 (1989).

The present invention provides recombinant materials and methods for producing D-amino acids, including enantiomerically-pure D-amino acids, specifically D-phenylalanine.

SUMMARY OF THE INVENTION

The present invention provides methods for producing D-amino acids and recombinant microorganisms which produce D-amino acids. Microorganisms produced according to the invention contain a D-aminotransferase gene (dat) capable of effectively catalyzing production of D-phenylalanine in *E. coli* and optionally a dadX gene (encoding an alanine racemase), free of natural regulation, either integrated on a host chromosome or on a plasmid.

In a preferred embodiment of the invention, methods for producing D-phenylalanine are provided, said methods comprising the steps of incorporating into a microorganism a gene encoding a D-aminotransferase; increasing phenylpyruvic acid production; culturing the microorganism; and isolating D-phenylalanine produced thereby.

In a preferred embodiment, an alanine racemase, preferably a deregulated alanine racemase, and means for eliminating L-aminotransferases encoded by aspC, tyrB, and ilvE are also incorporated into the microorganism. The resulting inability to produce L-transaminases results in the production of entaniomerically-pure D-phenylalanine.

The invention also provides methods for the production of enantiomerically-pure D-phenylalanine; wherein a microorganism is transformed or transfected with a gene encoding a D-aminotransferase and optionally means for increasing phenylpyruvic acid production; and wherein L-aminotransferase activity is reduced or preferably eliminated.

The present invention provides microorganisms which produce D-phenylalanine. In a preferred embodiment, a microorganism of the invention is an *Escherichia coli* which has been transformed or transfected with an exogenous D-aminotransferase gene; an exogenous alanine racemase gene, such as a dadX gene of *E. coli* K12; and an exogenous aroH gene to increase throughput to the amino acid biosynthetic pathway via chorismate. An *Escherichia coli* of the invention also may comprise a pheA 34 gene as provided in co-owned U.S. Pat. No. 5,120,837, incorporated by reference herein, wherein the pheA coding sequence encodes a protein which is substantially resistant to feedback inhibition. Preferred microorganisms according to the invention were deposited on Mar. 22, 1995 with the American Type Culture Collection, 12310 Parklawn Drive, Rockville, Md. 20852 under ATCC accession numbers ATCC 69765 and ATCC 69766.

The present invention also provides a novel DNA encoding a *B. sphaericus* D-aminotransferase, plasmids containing that DNA, and host cells comprising the plasmids.

The present invention also provides methods for producing D-phenylalanine comprising transforming or transfecting an appropriate host cell with DNA encoding an aspartate racemase and with DNA encoding a phosphoenolpyruvate carboxykinase (a pckA gene), wherein the cell medium is supplemented with L-aspartic acid. Phosphoenolpyruvate carboxykinase catalyzes production of phosphoenolpyruvate from oxaloacetate. Finally, the present invention provides a preferred medium for culturing cells of the invention, said medium comprising from 2–7 g/L aspartic acid. Additional aspects of the invention are apparent to the skilled artisan upon consideration of the following detailed description.

DETAILED DESCRIPTION OF THE INVENTION

The present invention provides materials and methods for the production of D-amino acids and specifically for the production of D-phenylalanine. In a method according to the invention, a D-aminotransferase gene is introduced into a bacterial cell where its gene product catalyzes a transamination reaction between D-alanine and phenylpyruvate to produce D-phenylalanine and pyruvate. D-alanine and phenylpyruvate are normally present in the cell, the former for incorporation into the cell wall, the latter as the last precursor in the pathway leading to L-phenylalanine biosynthesis. Introduction into the cell of a D-aminotransferase gene results in the production of D-phenylalanine as well as L-phenylalanine, as the D-aminotransferase competes for the substrate, phenylpyruvate, with the L-aminotransferases naturally present in the cell. However, by reducing, or preferably eliminating, L-aminotransferase activity or production, enantomerically-pure D-phenylalanine is produced by the microorganism. Production of enantiomerically pure D-phenylalanine is beneficial in reducing steps necessary for the isolation of D-phenylalanine from racemic mixtures.

In order to further increase D-phenylalanine production, phenylpyruvate production is increased in addition to reducing or eliminating the conversion of phenylpyruvate to L-phenylalanine. Also in a preferred embodiment, D-alanine levels may be increased in the cell in order to assure sufficiently high levels of D-alanine for both transamination and incorporation into the cell wall by, for example, the introduction of a gene encoding an alanine racemase, such as the dadX gene. A preferred D-aminotransferase for incorporation into *E. coli* is obtained from *Bacillus sphaericus*. Means for improving production and yield of D-phenylalanine may also be incorporated in cells and methods of the invention, including addition of an aroH gene to increase throughput to the aromatic amino acid biosynthetic pathway and a mutation in the dadA gene in order to inhibit degradation of D-alanine by eliminating activity of the dadA gene product, the D-amino acid dehydrogenase.

Example I provides details of the isolation and cloning of a D-aminotransferase-encoding DNA. Example II exemplifies production of vectors for use in recombinant expression of a D-aminotransferase. Example III shows construction of host cells for use according to the invention, and Example IV shows methods for increasing D-phenylalanine production through use of an aspartate racemase.

EXAMPLE I

Isolation of D-Aminotransferase DNA

Cultures of *Bacillus sphaericus*, ATCC Accession No. 10208, were obtained from the American Type Culture Collection as a source of D-aminotransferase DNA. Cultures were streaked on unsupplemented LB medium and allowed to grow overnight at 37° C. In order to prepare chromosomal DNA, a single colony was used to inoculate 50 ml Luria Broth in a 1 L flask which was shaken overnight at 300 rpm and 37° C. Cells were then harvested by centrifugation at 10,000 G for 5 minutes, washed in 0.85% saline and centrifuged again at 10,000 G for 5 minutes. The resulting pellet was resuspended in 5 ml of 10 mM glucose, 25 mM Tris HCl, pH 8.0, and 10 mM ethylenediamine tetraacetic acid (EDTA). An aliquot of 50 µl RNase A was added and the solution was mixed gently. Subsequently, 10 ml of 0.4% sodium dodecyl sulphate (SDS) and 100 µg/ml protease K were added to the mixed solution which was then incubated at 37° C. until clear. Sodium acetate, pH 5.2, was then added to a final concentration of 300 mM. Gentle phenol extractions were carried out using a volume of phenol approximately equal to the aqueous phase until no white precipitate was visible at the phase interface. The aqueous phase was then removed and the chromosomal DNA was precipitated using 2.5 volumes of ethanol. The DNA pellet was removed and resolubilized in 300 mM sodium acetate, pH 5.2. Ethanol precipitation was carried out and the DNA pellet was removed, dried and dissolved in 2 ml distilled water. The DNA concentration was determined to be 150 µg/ml. In addition to the procedure described above, standard procedures are known for the isolation of bacterial DNA and are reported, for example, in *Current Protocols in Molecular Biology*, 2.4.1–2.4.5 (Ausubel, et al., eds., 1994), incorporated by reference herein.

The chromosomal DNA obtained as described above was then partially digested with MboI. Ideal digestion, yielding fragments in the range of 2–10 kb, was obtained using 13 µg chromosomal DNA and digesting for 40 minutes with 2.5 U MboI (New England Biolabs, Beverly, Mass.). Approximately 13 µg of chromosomal DNA prepared as indicated above was partially digested with 2.5 U of MboI in a total volume of 100 µl at 37° C. in Biolabs MboI buffer. Samples of 17 µl were taken at 5, 10, 20, 30, 40, and a sample of 15 µl was taken at 50 minutes. All samples were heated to 65° C. in order to destroy any restriction enzyme present in the sample and then placed on ice. A 5 µl aliquot of each sample was electrophoresed on a 0.8% agarose gel using TBE buffer as described in Sambrook, et al. (eds.), *Molecular Cloning: A Laboratory Manual* (Cold Spring Harbor Laboratory Press): 6.3–6.62 (1989), incorporated by reference herein. From the electrophoresis data, it was determined that the sample taken at 40 minutes contained the majority of the DNA in the 2–10 kb size range and it was those fragments which were used to construct a library in plasmid pIF306 for expression of the D-aminotransferase.

Plasmid pIF306 is derived from pBR322. In order to construct pIF306, a modified pheA promoter was inserted between unique HindIII and SphI sites on pBR322. Within the HindIII to SphI insert there exists unique BamHI and BglII sites. The modified pheA promoter is derived from that characterized in co-owned U.S. Pat. No. 5,120,837, incorporated by reference herein, such that the sequence is as follows:

```
                                              (SEQ ID NO: 1)
HindIII         -35                    -10
AAGCTTTTTTGTTGACAGCGTGAAAACAGTACGGGTATAATACT BamHI     Start
AAAGTCACAAGGAGGATCCACTATGACATCGGAAAACCCGTTACT HaeII
GGCGCT.
```

Vector DNA was prepared by digesting pIF306 to completion with BamHI and BglII, each of which produces ends compatible with those produced by MboI. The digest was carried out at 37° C. in a total volume of 20 µl for 2 hours using 0.5 µg of plasmid DNA and 2 units of each enzyme. Fragments of 4.25 kb and 1.25 kb were produced and separated by electrophoresis on a 1% agarose TBE gel. The desired 4.25 kb fragment was excised from the gel and recovered using a Gel Extraction Kit (Qiagen Inc.). That fragment was then treated with calf intestinal phosphatase (New England Biolabs) at 37° C. for 1 hour in a volume of 20 µl with 1 unit of enzyme in Biolabs buffer #2 according to the manufacturer's instructions in order to dephosphorylate the ends of the DNA and to prevent recircularization. The mixture was then treated with a PCR purification kit (Qiagen) in order to isolate the DNA fragment free of enzyme.

The PIF306 vector fragment was ligated to the fragments from the 40 minute partial digest (see above) of ATCC 10208 chromosomal DNA by combining approximately 20 ng of vector fragment with the remaining approximately 12 µl of the 40 minute partial digest. Ligation was accomplished using a Takara Ligation Kit (Takara Biochemcials) according to the manufacturer's instructions. The ligation was carried out at 17° C. for 2 hours, at which time the DNA was recovered using a PCR purification kit (Qiagen) in a final volume of 50 µl.

The resulting plasmids were introduced into *E. coli*, XL1-Blue (Stratagene) by electroporation. Transformants were plated on LB medium supplemented with 50 µg/ml ampicillin. Approximately 20,000 transformants were produced and pooled. Plasmid DNA was then isolated as reported in *Molecular Cloning: A Laboratory Manual* (Sambrook, et al., eds. 2d ed. 1989), incorporated by reference herein. The resulting plasmid DNA was incorporated into *E. coli*, strain WM335 by electroporation using a Bio-Rad Gene Pulser™ set to 2.5 kv with 25 µF capacitance and a Bio-Rad pulse controller set to 200 ohms resistance. Strain WM335 may be obtained from the Phabagen Collection, Department of Molecular Cell Biology, State University of Utrecht, The Netherlands and is reported in Lugtenberg, et a., *J. Bacteriol.*, 114: 499–506 (1973), incorporated by reference herein. Cells were pulsed in BioRad Gene Pulser™ cuvettes with a 0.2 cm gap. *Escherichia coli* cells to be transformed were grown (50 ml cultures) to an optical density of 0.7 at 600 nm. The cells were then recovered by centrifugation at 10,000 g for 5 minutes and washed in 30 ml deionized distilled water. The cells were re-spun and re-suspended in 200 µl deionized distilled water and 40 µl of cells were combined with 10 µl of the recovered ligation mix and placed in an electroporation cuvette. A single pulse was applied to the cuvette and 500 µl SOC medium (GIBCO/BRL, Gaithersburg, Md.) was added and mixed with the cell suspension. The contents of the cuvette were then transferred to a 20 ml pvc tube and incubated for 30 minutes at 37° C. Cells were then plated on appropriate media and selected as described below. Numerous means for transforming/transfecting DNA into microorganisms are known and may be used in methods according to the invention. See, e.g., Chang, et al. (eds.), *Guide to Electroporation and Electrofusion* (Academic Press, 1992).

Figure 1:
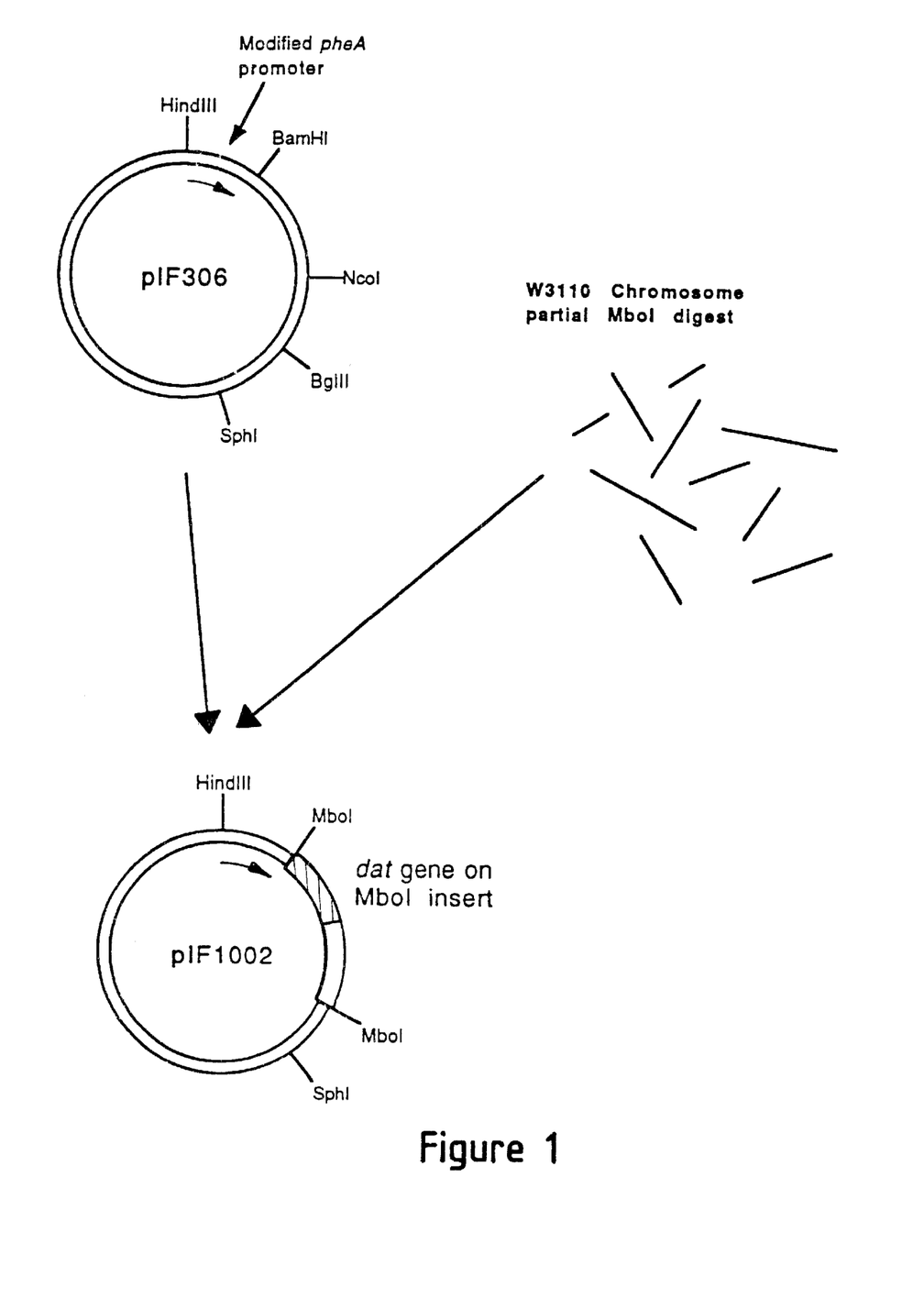
FIG. 1 is a schematic diagram showing construction of plasmid pIF1002.

Transformants were plated on LB medium supplemented with 50 µg/ml thymine and 60 µg/ml ampicillin but lacking D-glutamate. Only those transformants able to make D-glutamate survive on that medium. According to reports in the literature, all such cells should have necessarily been transformants carrying the dat gene of *B. sphaericus* because *B. sphaericus* was thought to lack a glutamate racemase. However, two different classes of transformants were isolated by the procedure described above, one carrying the dat gene and the other carrying a glutamate racemase. The racemase-containing clone was designated pIF1001 and the dat-containing clone was designated pIF1002. FIG. 1 is a schematic diagram showing construction of pIF1002.

In each case, the clones were mapped by restriction endonuclease digestion and the genes were sequenced. The sequence of the dat gene and the deduced amino acid sequence of the encoded protein are shown in SEQ ID NOS: 2 and 3. It was found that the dat gene had a high degree of sequence homology with the only other known dat gene sequence. See Tanizawa, et al., *J. Biol. Chem.,* 264: 2450–2454 (1989). However, the C-terminal amino acid sequence of the D-aminotransferase encoded by the *B. sphaericus* dat gene in pIF1002 did not agree with that of the only other published report a *Bacillus sphaericus* D-aminotransferase in which only a C-terminal sequence was published. That sequence, reported in *Transaminases,* Christen, et al. (eds.), 464 (1985) is Val-Ile-(Phe-Tyr)-Leu-Ala-Leu (SEQ ID NO: 4). In contrast, the correct C-terminal sequence as provided in the present invention is Leu-Pro-Ile-Ser-Ile-Asn-Ala (SEQ ID NO: 5). The present inventors attempted, without success, to use the sequence reported in Christen in order to isolate a *B. sphaericus* D-aminotransferase-encoding gene.

Both clones were then subjected to a biological assay for the presence of the dat gene. That assay is reported in *Methods in Enzymology,* 113: 108–113 (19), incorporated by reference herein. Briefly, cultures of pIF1001 or pIF1002 in WM335 cells were set up in 50 ml of LB medium supplemented with 50 μg/ml thymine and 200 μg/ml ampicillin. The cultures were grown overnight in 500 ml flasks in a shaking incubator at 37° C. Cells were harvested by centrifugation at 10,000 G for 5 minutes and washed in 50 mM potassium phosphate at pH 8.5. The cells were respun and taken up in 1 ml 50 mM potassium phosphate at pH 8.5. The cells were then lysed using a French Pressure Cell at 1000 lbs/in$^2$ and the lysates were centrifuged at 14,000 G in a microfuge for 30 minutes, at which time supernatant was extracted by micropipette. The resulting cell extracts were assayed using a lactate-dehydrogenase coupled assay as reported in *Methods in Enzymology*, 113: 108–113 (19), incorporated by reference herein. The assay mixture contained 0.3 M potassium phosphate, pH 8.5, 25 mM D-Alanine, 25 mM α-keto-glutarate, 0.1 mM NADH, 70 μg/ml lactate dehydrogenase and 50 μl cell extract. The reaction was started by addition of the NADH and lactate dehydrogenase to the other components in a 1 ml cuvette at 25° C. The reaction produced a change in absorbance at 338 nm as evidence of oxidation of NADH. To correct for non-specific oxidation, control assays were run using an assay mixture lacking cell extract. As an additional control, assays were run using an assay mixture lacking D-alanine. Extracts of untransformed WM335 cells and controls produced essentially identical changes in absorbance; whereas WM335 cells bearing pIF1002 showed changes in absorbance in excess of 30-fold greater than controls. The dat-containing clone had levels of activity about 100-fold greater than extracts of *B. sphaericus*, a consequence of overexpression on the high copy number plasmid, pIF306. Plasmid pIF1001 had activity identical to that of the controls.

EXAMPLE II

Construction of a Vector for D-Phenylalanine Production

In order to construct a vector which enables production of D-phenylalanine in a host cell, the dat gene was isolated from pIF1002 using PCR. Amplification of the dat-encoding region was accomplished using an Amplitaq™ PCR Kit (Perkin-Elmer) in a 0.2 ml MicroAmp™ reaction tube (Perkin-Elmer, Norwalk, Conn.) to which was added 100 ng pIF1002 DNA (1 μl); 5 μl each of primers, MB1809 5' CGCAGATCTACTATGGCATACTCATTATGG 3' (SEQ ID NO: 6); and MB1810 5' CATGCCATGGATCCTCCTTT-TAGGTAGCTCTTTTTAATC 3' (SEQ ID NO: 7) at a concentration of 10 nanomoles/ml each; 2 μl each of dATP, dCTP, dTTP, and dGTP (10 mM each); 10 μl buffer comprising 15 mM MgCl$_2$, 500 mM KCl$_2$, 100 mM Tris (pH 8.3), and 0.01% gelatin; a Taq DNA polymerase (0.5 μl at 5 u/μl, Amplitaq™); and distilled water to a total volume of 100 μl. The tube was capped and placed in a Perkin Elmer 9600 Thermal Cycler; Amplification was carried out by pre-heating at 94° C. for 3 minutes, followed by 25 cycles of denaturation at 94° C. for 30 seconds, annealing at 50° C. for 30 seconds, and extension at 72° C. for 90 seconds. The reaction mixture was stored at 4° C.

Figure 2:
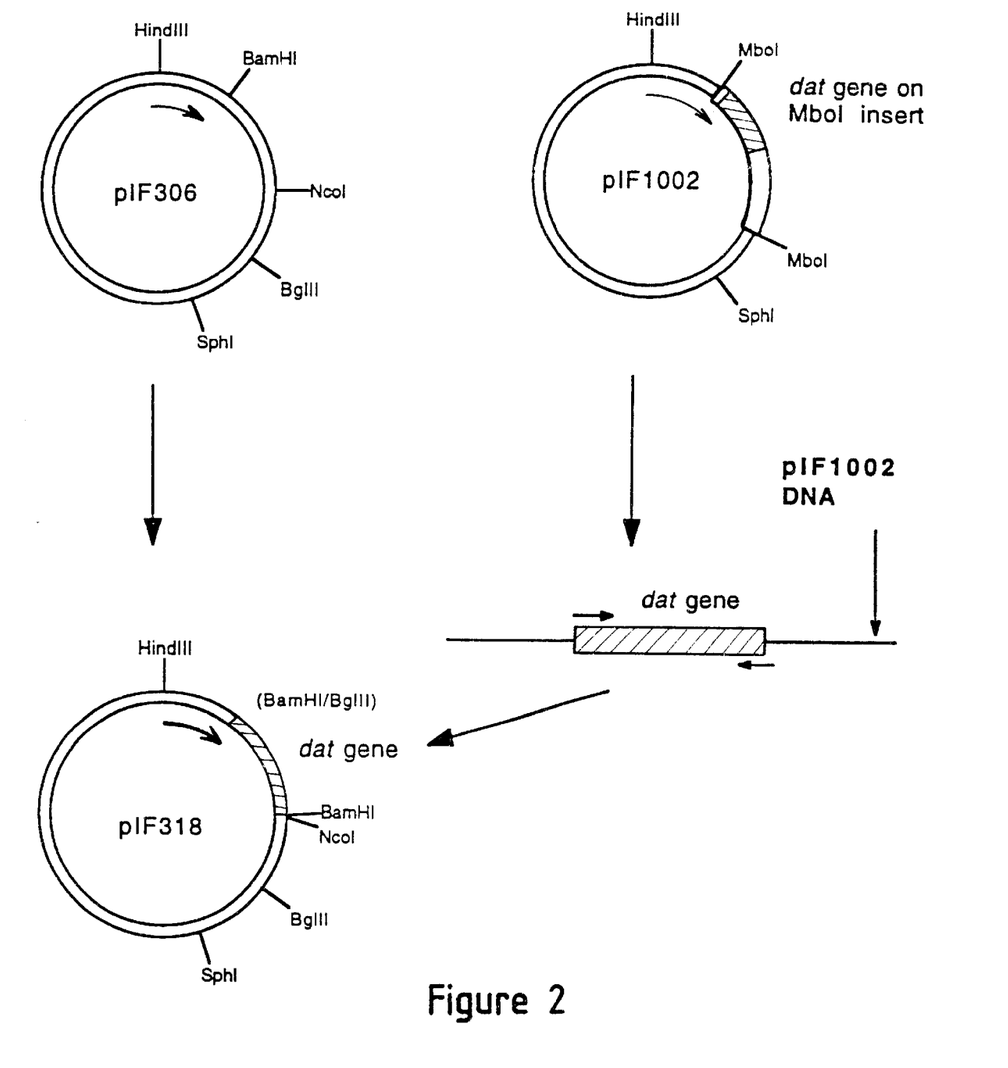
FIG. 2 is a schematic diagram showing construction of plasmid pIF318.
Figure 3:
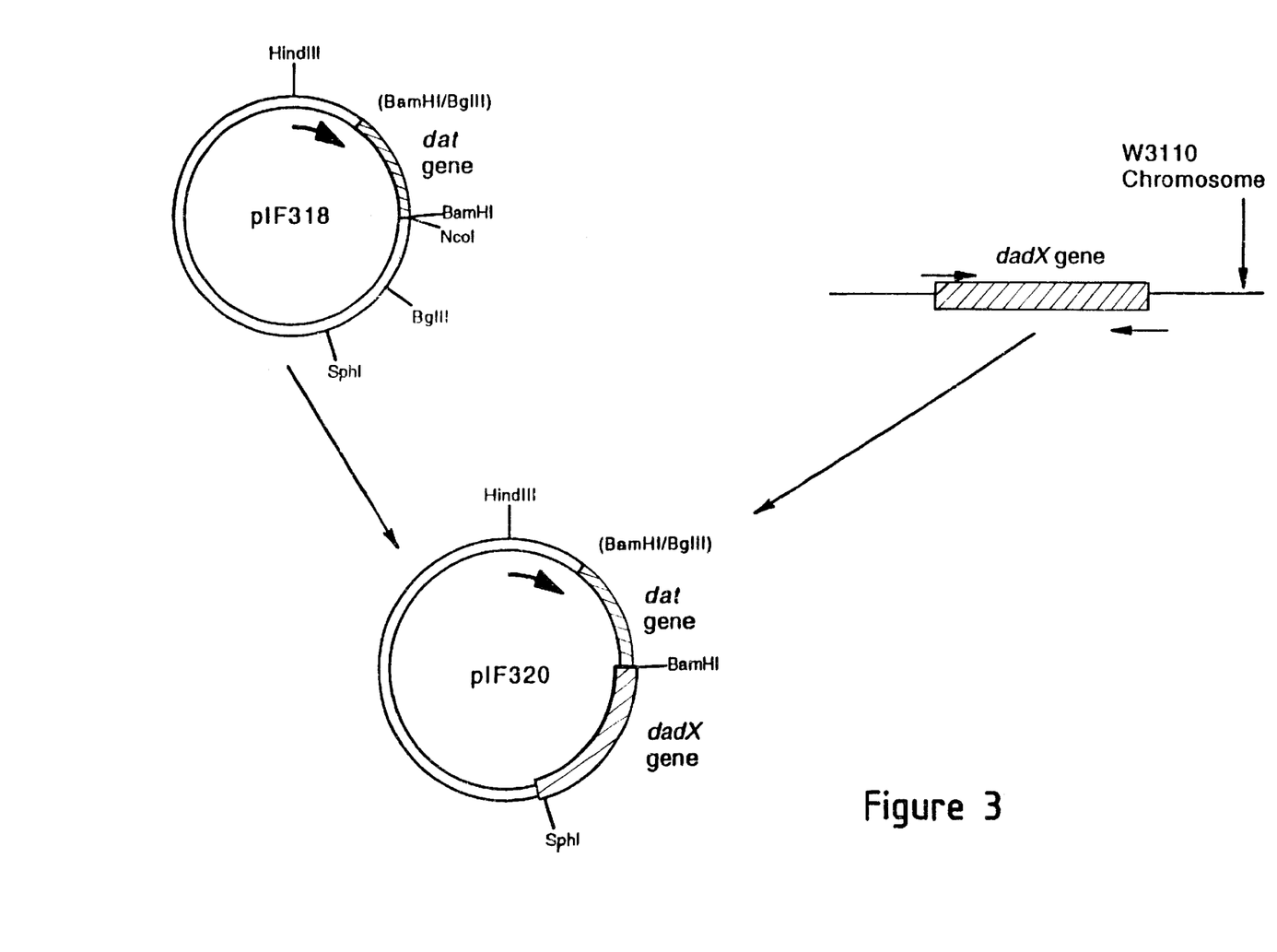
FIG. 3 is a schematic diagram showing construction of plasmid pIF320.

The resulting approximately 914 bp PCR product was digested with BglII and NcoI and the product was then ligated into the 4.5 kb BamHI to NcoI fragment of pIF306 using ligation conditions described above and a Ligation Kit (Takara Biochemicals) according to the manufacturer's instructions. The resulting plasmid was designated pIF318. Construction of pIF318 is shown in FIG. 2. That plasmid was then cleaved with BamHI and SphI for the insertion of a dadX gene. The MB1810 primer referred to above contains a BamHI site (GGATCC) which overlaps the NcoI site in that primer. It is the BamHI site (and the downstream SphI site) that is used for introduction of dadX to form a synthetic operon comprising dat and dadX. The dadX gene sequence was obtained from the Genbank database, reference code ECODADX. From that sequence, PCR primers MB1811, 5' CGCGGATCCACTATGACCCGTCCGATACAGGCC 3' (SEQ ID NO: 8) and MB1816, 5' TGCCATGCATGCCTA-CAGTTGCTGACCAGCCGG 3' (SEQ ID NO: 9) were designed and used to isolate the dadX gene from *E. coli* strain W3110 (ATCC 27325). Amplification conditions were exactly as described above. The gene was isolated without its native promoter and ligated immediately downstream of the dat gene insert. Amplification result in an approximately 1171 bp fragment which was cleaved with BamHI and SphI and ligated to pIF318 which was similarly digested to form an approximately 4.8 kb fragment. The resulting plasmid was designated pIF320 and carries the dat and dadX genes in a synthetic operon. Construction of pIF320 is shown in FIG. 3.

An additional plasmid, designated pIF321 was then constructed. That plasmid contained dat and dadX genes of pIF320 isolated on a HindIII-to-SphI fragment (HindIII-promoter-dat-dadX-SphI) and ligated into pIF319, which contains the above-described pheA34 allele along with the aroH gene which encodes the tryptophan-dependent DAHP synthase of *E. coli*.

The pIF319 plasmid is based upon the pLG338 plasmid disclosed in co-owned U.S. Pat. No. 5,354,672, incorporated by reference herein, with the kanamycin resistance marker replaced by a chloramphenicol resistance marker to avoid conflict with a potential host strain, *E. coli* HW857, which carries a kanamycin resistance gene. Plasmid pIF319 contains the pheA34 gene, as disclosed in co-owned U.S. Pat. No. 5,120,837, incorporated by reference herein, and the aroH gene in a synthetic operon between unique EcoRI and SalI sites in pLG338. The pheA34 allele contains a modification in the pheA coding sequence which substantially reduces phenylalanine-mediated feedback inhibition of the enzyme. It also contains a deregulated version of the pheA promoter region which lacks the attenuator sequence and allows increased expression of associated genes (See above). The presence of pheA34 and aroH effectively deregulate pathways to phenylpyruvate in *E. coli* W3110 and in any *E. coli* K12 strain. Plasmid pIF319 may also be derived from pJN307, disclosed in U.S. Pat. No. 5,120,837, by introduction of the *E. coli* aroH gene between unique BamHI and SalI sites in pJN307 followed by introduction of the *E. coli* aspC promoter into the BamHI site. The aroH gene is isolated from the *E. coli* W3110 by PCR using primers 5' CGCGGATCCTCGTCATGAACAGAACT-GACGAACTCCG 3' (SEQ ID NO: 10) and 5' ACGCGTC-GACTCAGAAGCGGGTATCTACCGCAGAGG 3' (SEQ ID NO: 11). The resulting PCR fragment is cleaved with BamHI and SalI and ligated to the 8 kb fragment generated by similar cleavage of pJN307. The aspC promoter region is then inserted at the unique BamHI site in the resulting intermediate plasmid. The aspC promoter region is isolated from *E. coli* W3110 by PCR using primers 5' GGAA-GATCTTACATCATCAACCAGATCGATTCTG 3' (SEQ ID NO: 12) and 5' CGCGGATCCATTATGGTTACA-GAAGGGAAGTCC 3'(SEQ ID NO: 13). The resulting approximately 278 bp fragment is then cleaved with BglII and BamHI and ligated to the vector cleaved at a unique BamHI site. The resulting ligation results in a DNA sequence that cannot be cleaved with BglII and only singly with BamHI and, therefore, provides a simple means for verification of the orientation of the aspC promoter. The resulting construction is pJN326. Plasmid pJN319 is generated from pJN326 by deletion of most (520 bp) of the kanamycin resistance gene by cleavage with HindIII and XhoI and insertion of a DNA fragment encoding the chloramphenicol resistance gene of pHSG415. The chloramphenicol resistance gene of pHSG415 is isolated by PCR using the primers 5'CCGCTCGAGCCCGACG-CACTTTGCGCCGA 3' (SEQ ID NO: 14) and 5' CCCAAGCTTATCAGGCTCTGGGAGGCAG 3' (SEQ ID NO: 15). The resulting approximately 1191 bp fragment is cleaved with HindIII and XhoI and ligated to the 8.87 kb fragment generated by similar cleavage of pJN326. The resulting plasmid is pIF319.

Figure 4:
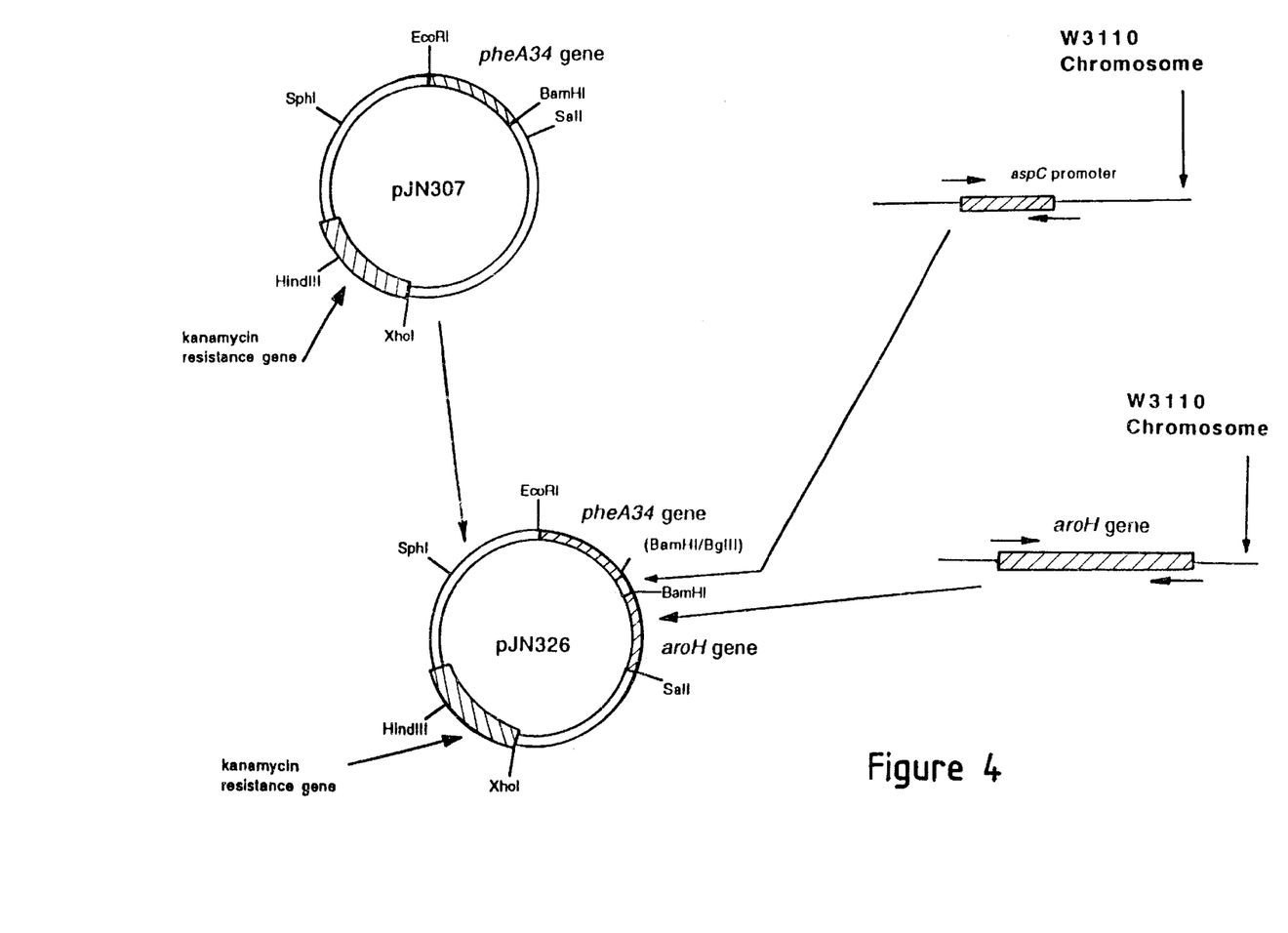
FIG. 4 is a schematic diagram showing construction of plasmid pJN326.
Figure 5:
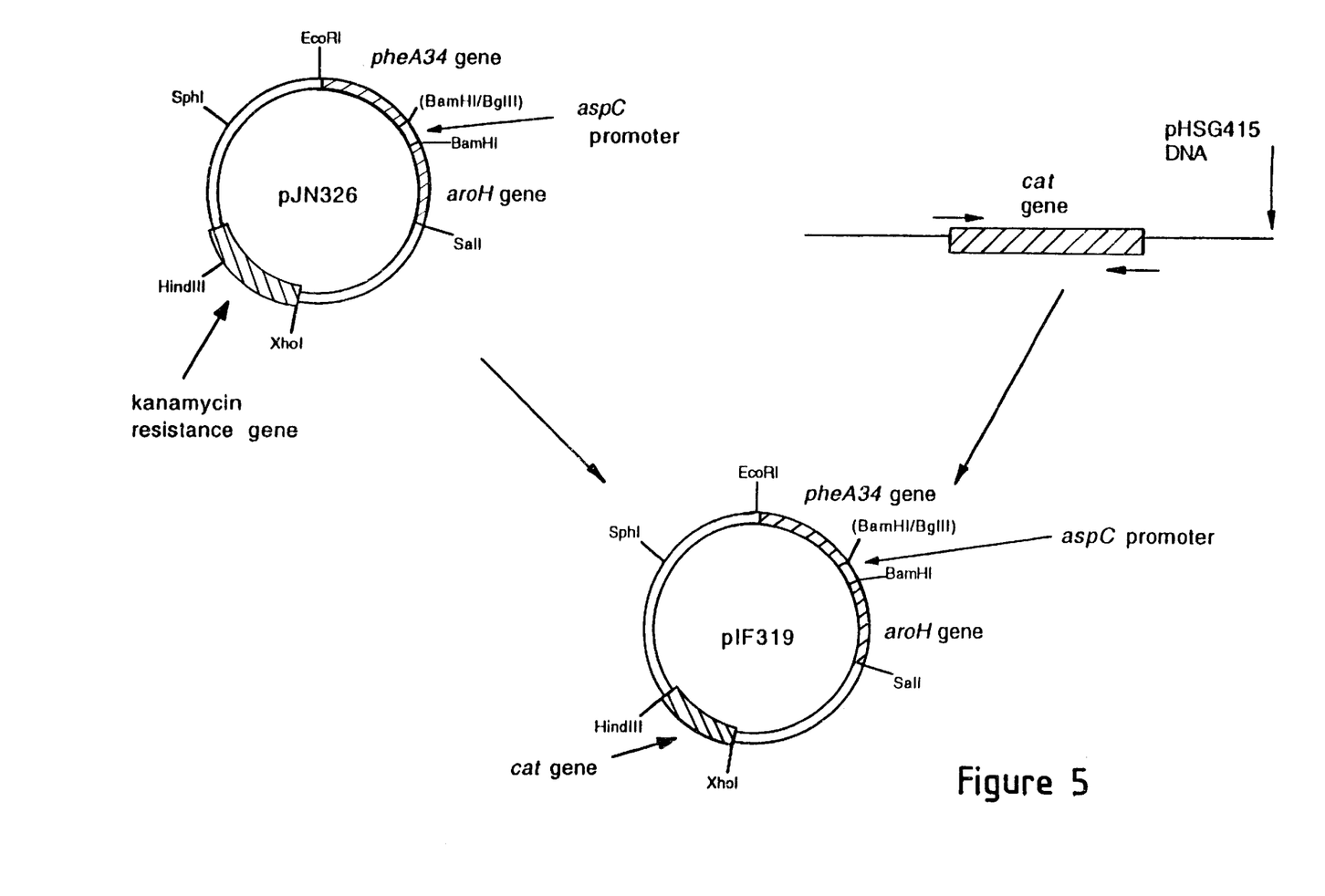
FIG. 5 is a schematic diagram showing construction of plasmid pIF319.
Figure 6:
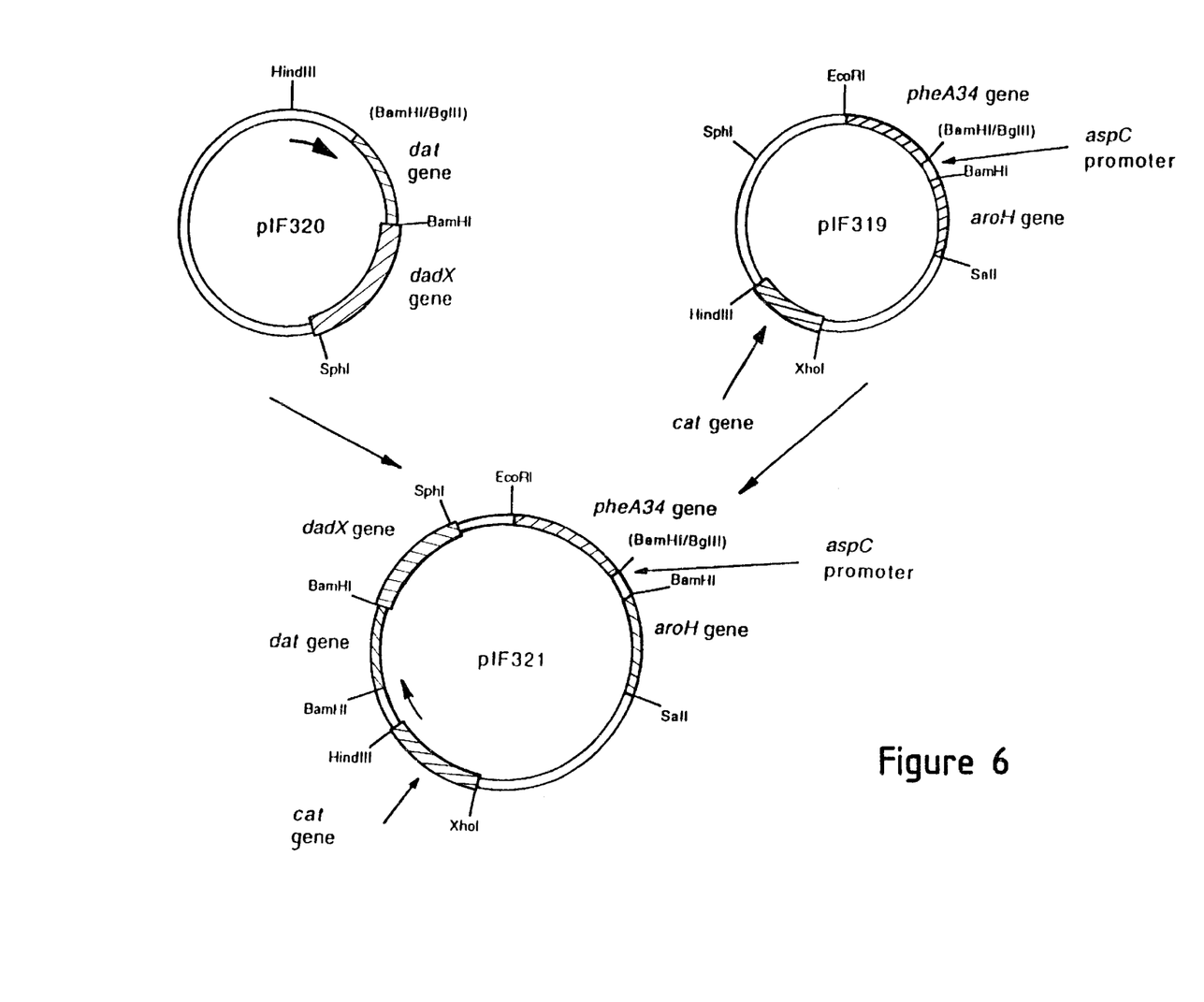
FIG. 6 is a schematic diagram showing construction of plasmid pIF321.

Plasmid pIF321 is generated by cleaving pIF320 with HindIII and SphI and isolating the 2.1 kb fragment carrying the dat and dadX genes which is then ligated to the 9.2 kb fragment produced by similar cleavage of pIF319. Construction of pJN326, pIF319, and pIF320 are shown in FIGS. 4–6, respectively.

EXAMPLE III

Preparation of D-Phenylalanine-Producing Host Cells

Several host cells were used for incorporation of the above-described plasmids. Any of the plasmids described above may be incorporated into a suitable host cell for production of D-phenylalanine. Incorporation of any of the above-described plasmids into host cells which either partially or completely lack the ability to make L-transaminases, results in the production of either partially, or completely-enantiomerically pure D-phenylalanine. Strains partially or completely deficient in L-phenylalanine transaminases (ilvE, aspC, and tyrB) may be derived, from transaminase mutants available in stock centers, such as the American Type Culture Collection or the *E. coli* Genetic Stock Center, using common genetic methods, such as are described, for example, in Miller, *A Short Course In Bacterial Genetics,* incorporated by reference herein. Several examples, demonstrating production of D-phenylalanine according to the invention, are presented below.

*Escherichia coli* strain W3110 (ATCC 27325) was initially used as a host strain for plasmids according to the invention. Three strains were used to test the efficacy of methods and strains according to the invention under different nutrient conditions. *Escherichia coli* strain PT100 is a strain which lacks all three genes encoding the aromatic amino acid transaminases (ilvE, aspC, and tyrB). Thus, PT100 requires tyrosine, aspartic acid, and phenylalanine, as well as valine, leucine, and isoleucine. Moreover, PT100 cannot make D-phenylalanine because it lacks the dat gene. Other strains may be used wherein the L-transaminases have been inactivated by, for example, site-directed mutagenesis. Recombinant strain RY352 is an *E. coli* mutant which comprises PT100 carrying plasmids pIF1002 and pIF321 as described above. That strain carries the dat gene as well as the dadX gene (encoding an alanine racemase) and aroH in order to increase throughput to chorismate and ultimately the aromatic amino acids. Finally, RY352 contains the pheA34 allele. Strain RY347 is identical to RY352 except that RY347 has a mutation which renders the dadA gene nonfunctional. That gene normally encodes D-amino acid dehydrogenase which degrades D-alanine and D-phenylalanine. Strain RY347 and strain RY352 were deposited with the American Type Culture Collection, 12301 Parklawn Drive, Rockville, Md. 20852, on Mar. 22, 1995 as accession numbers ATCC 69766 and ATCC 69765, respectively. Means for generating strains containing a dadA mutation are known in the art and include, for example, site-directed mutagenesis. Additionally, it has been determined that host cells comprising only pIF321 show significant increases in D-phenylalanine as compared with untransformed host cells.

Each of the three above-mentioned strains was grown under four different growth conditions. In each case, growth medium consisted of 1.7 g/l potassium phosphate (dibasic), 2.0 g/l potassium phosphate (monobasic), 4.0 g/l ammonium phosphate, 0.24 g/l ferric ammonium citrate, 1.0 g/l calcium carbonate and 1.0 g/l magnesium sulphate.7 $H_2O$ in water to 930 ml at pH 7.2 sterilized for 20 minutes in an autoclave at 15 lb/in². After sterilization, the following were added: 35 g/l dextrose, 5 g/l L-aspartic acid, 5 g/l casamino acids, and 100 µg/ml each of L-tyrosine, L-phenylalanine, L-leucine, and L-valine. In addition, plasmid-bearing strains contained 10 µg/ml chloramphenicol, and 100 µg/ml ampicillin. Each of the strains was grown on unsupplemented medium, on medium supplemented with L-alanine, on medium supplemented with phenylpyruvate, and on medium supplemented with both L-alanine and phenylpyruvate (PPA), both at 1 mg/ml.

It was surprisingly found that recombinant cells according to the present invention grew better in medium comprising 5 g/L aspartic acid instead of the 100 µg/ml traditionally used in defined media. Such high concentrations of aspartic acid also allowed a reduction in the amount of other amino acids normally used in the medium, thus facilitating detection and isolation of D-phenylalanine produced by recombinant cells of the invention. For example, isoleucine has an HPLC peak which coincides with that of D-phenylalanine making isolation of D-phenylalanine more difficult. While D-phenylalanine produced by cells of the invention may be isolated using standard medium, use of a medium comprising 5 g/L aspartic acid allowed more rapid and distinct isolation of D-phenylalanine. Increasing the concentration of other amino acids, such as glutamate, proline, alanine, and cysteine failed to produce the increased growth rate of recombinant cells which was observed when aspartic acid concentration were increased. The use of a standard culture medium in which aspartic acid levels are increased provides an improvement in methods according to the invention because the increased growth rate obtained leads to increased D-phenylalanine production and increased ease of isolation of D-phenylalanine. A range of aspartic acid concentration from about 2 g/L to about 7 g/L is expected to produce observed increases in growth and yield. A preferred medium according to the invention comprises 2 to 7 g/L aspartate, about 5 g/L casamino acids (instead of the usual 20 g/L), and about 100 µg/ml each of L-tyrosine, L-phenylalanine, L4eucine, and L-valine. Other components as previously discussed herein are also added.

Each strain was grown as a 30 ml culture at 32° C. in a 250 ml culture flask placed in a shaking incubator at 300 rpm. Data provided herein are expressed in micrograms per O.D. 600 which equalized the number of cells in each culture and provides a basis for cross-culture comparisons. Following 24 hours of growth, 1 ml of culture was centrifuged at 14,000 G for 1 minute in a benchtop microfuge. The supernatant was decanted and the cells were discarded. Supernatant was passed through an Acrodisc 0.45 µm PVDF filter (Gelman) and a Microcon™ 10 microconcentrator of 10,000 D cutoff (Amicon). A 500 µl sample was submitted for analysis using HPLC in order to determine the mount of secreted D-phenylalanine. The results are presented in Table I below.

TABLE I

| SAMPLE | STRAIN | D-PHE (UG/ML/OD) |
|---|---|---|
| A | PT100 No additions | Undetectable |
| B | PT100 + L-alanine | Undetectable |
| C | PT100 + PPA | Undetectable |
| D | PT100 + L-alanine + PPA | Undetectable |
| E | RY352 No additions | 6.3 |
| F | RY352 + L-alanine | 6.3 |
| G | RY352 + PPA | 25.6 |
| H | RY352 + L-alanine + PPA | 17.9 |
| I | RY347 No additions | 34.1 |
| J | RY347 + L-alanine | 41.9 |
| K | RY347 + PPA | 64.7 |
| L | RY347 + PPA + L-alanine | 96.2 |

As shown in the table, strains in which the dat gene was incorporated (E-H) produced a greater amount of D-phenylalanine than control strains (A-D) under all four medium conditions. Addition of the dadA mutation resulted in even greater increases in D-phenylalanine production by transformed cells as compared to controls under all four medium conditions. As mentioned previously, host cells containing only pIF321 also displayed increased levels of D-phenylalanine. However, increasing dat gene levels by also transforming host cells with pIF1002 (in addition to pIF321) provides even greater increases in D-phenylalanine production as shown above.

EXAMPLE IV

Use of Aspartate Racemase and PEP Carboxykinase in Production of D-Phenylalanine L-aspartic acid may also be used as an amino donor in recombinant means for production of D-phenylalanine according to the present invention. There are two principal benefits to using L-aspartic acid instead of L-alanine as an amino donor in D-phenylalanine biosynthesis. First, L-aspartic acid is less expensive than L-alanine. Second, transamination of aspartic acid produces oxaloacetate which, in turn, is converted to phosphoenolpyruvate (PEP) by PEP carboxykinase. Phosphoenolpyruvate is a substrate for DAHP synthase and thereby a direct precursor in the aromatic amino acid biosynthetic pathway, resulting in formation of phenylpyruvic acid, the immediate precursor of phenylalanine. Accordingly, supplementation of the medium with L-aspartic acid provides an inexpensive substrate for transamination to D-phenylalanine (when the proper recombinant genes are provided in E. coli host cells) and increases the supply of phenylpyruvic acid, thus increasing substrate for D-phenylalanine synthesis.

In order for cells to utilize L-aspartic acid in the recombinant biosynthesis of D-phenylalanine, the host cell must be provided with an enzyme for conversion of L-aspartic acid to D-aspartic acid. That enzyme, aspartate racemase, has been isolated and cloned from *Streptococcus thermophilus* (IAM10064) and the DNA sequence of the gene encoding aspartate racemase may be obtained from the GENBANK database as entry STASPRAC. Based upon that gene sequence, the gene encoding aspartate racemase may be obtained from *S. thermophilus* by PCR amplification using the primers 5'GGAAGATCTACTATG-GAGAATTTTTTCAGTATTTTAGG3' (SEQ ID NO: 16) and 5'GCGGGATCCTCCTTTTCTACTTTTCA-GATACTGTATCTAATGC3' (SEQ ID NO: 17). The approximately 760 bp fragment generated is cleaved with BglII and BamHI and ligated to an approximately 11.3 kb linearized vector generated by partial BamHI cleavage of pIF321. The aspartate racemase gene is inserted in between dat and dadX in an orientation such that it is expressed colinearly with dat. Verification is achieved by cleavage of the ligation product with BamHI and SphI which produces fragments of 7.5 kb, 3.4 kb, and 1.116 kb. The resulting ligation of the BglII and BamHI ends between the dat and aspartate racemase genes results in a DNA which cannot be recleaved by either enzyme.

The aspartate racemase-containing plasmid is then partially cleaved with BamHI and the approximately 12 kb linearized vector which results is ligated to a PCR-generated fragment which contains the pckA gene. That gene, which encodes PEP carboxykinase, is obtained from GENBANK as ECOPCKA and is isolated from *E. coli* W31 10 by PCR using primers 5'GGAAGATCTACTATGCGCGTTAA-CAATGGTTTGACC3' (SEQ ID NO: 18) and 5'GCGG-GATCCTCCTTTGGGCCCTTATCCAGC-GAACCGTGAGATGC G3' (SEQ ID NO: 19). The resulting approximately 1428 bp fragment is cleaved with BglII and BamHI and ligated to the 12 kb linearized vector fragment described above. Insertion of the pckA gene at the BamHI site between the aspartate racemase gene and dadX in an orientation consistent with co-linear expression with dat and aspartate racemase is verified by digestion with BamHI and SphI which will produce fragments of approximately 8.9 kb, 3.4 kb, and 1.116 kb. The dadX gene may be deleted from the resulting vector by cleavage to completion with ApaI, generating fragments of 11.7 kb and 1716 bp, the smaller of which contains the dadX gene. Religation of the 11.7 kb fragment results in an intact vector without dadX.

Cells bearing the above plasmid are capable of utilizing L-aspartic acid from the growth medium in order to produce D-phenylalanine through expression of the recombinant aspartate racemase and D-aminotransferase genes.

The present invention has been described in terms of its preferred embodiments. Numerous modifications are apparent to the skilled artisan upon consideration of the foregoing. Accordingly, the invention is only limited by the proper scope of the claims.

We claim:

1. A method for producing D-phenylalanine in an *Escherichia coli*, comprising the steps of:
   incorporating into an *Escherichia coli* microorganism a gene encoding a *Bacillus sphaericus* D-aminotransferase;
   culturing said microorganism in a culture medium; and
   isolating D-phenylalanine from said culture medium.

2. The method according to claim 1, wherein said *Escherichia coli* lacks functional aspC, ilvE, and tyrB genes.

3. The method according to claim 1, further comprising the step of:
   incorporating into said microorganism a gene encoding an alanine racemase.

4. The method according to claim 1, further comprising the step of incorporating into said *Escherichia coli* a dadX gene.

5. The method according to claim 1, further comprising the step of introducing a dadA gene mutation in said *Escherichia coli* such that said dadA gene is nonfunctional.

6. The method according to claim 1, further comprising the step of incorporating into said *Escherichia coli* an aroH gene.

7. A method for producing enantiomerically-pure D-phenylalanine in *Escherichia coli*, comprising the steps of:
   incorporating into an *Escherichia coli* a gene encoding a *Bacillus sphaericus* D-aminotransferase;
   further incorporating into said *Escherichia coli* a gene selected from the group consisting of genes encoding aspartate racemase and phosphoenolpyruvate carboxykinase;
   eliminating activity of aspC, tyrB, and ilvE in said *Escherichia coli*;
   culturing said *Escherichia coli* in a culture medium; and
   isolating D-phenylalanine from said culture medium.

8. The method according to claim 7, further comprising the step of introducing into said *Escherichia coli* a dadX gene.

9. The method according to claim 7, wherein said further incorporating step comprises introducing an aroH gene into said *Escherichia coli*.

10. The method according to claims 1 or 7, wherein said culture medium comprises from about 2 to about 7 g/L aspartic acid.

11. A method for producing D-phenylalanine in *Escherichia coli*, comprising the steps of;
    eliminating the activity of aspC, tyrB, and ilvE genes in an *Escherichia coli*;
    incorporating in said *Escherichia coli* DNA encoding an aspartate racemase;
    further incorporating in said *Escherichia coli* DNA encoding a *Bacillus sphaericus* D-aminotransferase;
    culturing said *Escherichia coli* in a culture medium comprising from about 2 to about 7 g/l aspartic acid; and
    isolating D-phenylalanine from said culture medium.

12. The method according to claim 11, further comprising the step of incorporating into said *Escherichia coli* a pckA gene.

\* \* \* \* \*